United States Patent [19]

Charbonneau

[11] Patent Number: 5,500,206

[45] Date of Patent: Mar. 19, 1996

[54] ORAL COMPOSITIONS COMPRISING ACTINOMYCES VISCOSUS FIMBRIAE

[75] Inventor: Duane L. Charbonneau, Middletown, Ohio

[73] Assignee: The Procter & Gamble Company, Cincinnati, Ohio

[21] Appl. No.: 236,911

[22] Filed: Apr. 29, 1994

[51] Int. Cl.$^6$ .............................. A61K 7/28; A61K 7/16; A61K 7/18

[52] U.S. Cl. ................. 424/50; 424/49; 424/52; 514/835

[58] Field of Search ............... 514/835; 424/50, 424/52, 49

[56] References Cited

U.S. PATENT DOCUMENTS

| | | | |
|---|---|---|---|
| 4,268,434 | 5/1981 | Higerd et al. | 260/112 |
| 4,454,109 | 6/1984 | Hillman | 424/50 |
| 4,581,227 | 4/1986 | Kjelleberg et al. | 424/49 |
| 4,659,561 | 4/1987 | Fives-Taylor et al. | 424/48 |
| 4,661,350 | 4/1987 | Tsurumizu et al. | 424/92 |
| 4,891,210 | 1/1990 | Norris | 424/50 |
| 4,939,123 | 7/1990 | Neeser et al. | 514/8 |
| 4,957,686 | 9/1990 | Norris | 424/50 |
| 5,013,542 | 5/1991 | Hay et al. | 424/54 |
| 5,198,352 | 3/1993 | Nesser et al. | 435/101 |
| 5,202,113 | 4/1993 | London | 424/54 |
| 5,240,704 | 8/1993 | Tsurumizu et al. | 424/85.8 |
| 5,288,617 | 2/1994 | Mattick et al. | 424/88 |

FOREIGN PATENT DOCUMENTS

| | | |
|---|---|---|
| 148025 | 7/1985 | European Pat. Off. . |
| 92/06191 | 4/1992 | WIPO . |

OTHER PUBLICATIONS

Clark, W. B., J. E. Beem, W. E. Nesbitt, J. O. Cisar, C. C. Tseng and M. J. Levine, "Pellicle Receptors for *Actinomyces viscosus* Type 1 Fimbriae In Vitro", *Infection and Immunity*, vol. 57, No. 10 (1989), pp. 3003–3008.

Gibbons, R. J. and D. I. Hay, "Human Salivary Acid Proline–rich Proteins and Statherin Promote the Attachment of *Actinomyces viscosus* LY7 to Apatitic Surfaces", *Infection and Immunity*, vol. 56, No. 2 (1988), pp. 439–445.

Gibbons, R. J., D. I. Hay and D. H. Schlesinger "Delineation of a Segment of Adsorbed Salivary Acidic Proline–rich Proteins Which Promotes Adhesion of *Streptococcus godonii* to Apatitic Surfaces", *American Society for Microbiology*, vol. 59 (1991), pp. 2948–2954.

Hasty, D. L., I. Ofek, H. S. Courtney and R. J. Doyle, "Multiple Adhesins of Streptococci", *Infection and Immunity*, vol. 60, No. 6 (1992), pp. 2147–2152.

Hay, D. I., R. J. Gibbons, S. K. Schluckebier, M. S. Ferland, and D. H. Schlesinger "A Sequence in Salivary Acidic Proline–rich Proteins which Mediates Adhesion of *Actinomyces viscosus* LY7 to Hydroxyapatite", *J. Dental Rearch*, vol. 69, p. 268.

Murray, P. A., A. Prakobphol, T. Lee, C. I. Hoover and S. J. Fisher "Adherence of Oral Streptococci to Salivary Glycoproteins", *Infection and Immunity*, vol. 60, No. 1 (1992), pp. 31–38.

Wheeler, T. T. and W. B. Clark "Fibril–mediated Adherence of *Actinomyces viscosus* to Saliva–treated Hydroxyapatite", *Infection and Immunity*, vol. 28, No. 2 (1980), pp. 577–584.

Willcox, M. D. P. and K. W. Knox "A Comparison of the Adhesion Profiles and Cell Surface Characteristics of *Streptococcus mitis* with those of Other Members of the *Streptococcus sanguis* Group" *Microbial Ecology in Health and Disease*, vol. 4 (1991), pp. 61–72.

Primary Examiner—Ronald W. Griffin
Attorney, Agent, or Firm—Betty J. Zea; Karen F. Clark; Jacobus C. Rasser

[57] ABSTRACT

The present invention relates to compositions and methods for inhibiting or preventing growth of dental plaque on tissues within the human oral cavity comprising topical administration, to tissues of a human oral cavity, of a composition comprising a safe and effective amount of *Actinomyces viscosus* fimbriae.

20 Claims, No Drawings

ORAL COMPOSITIONS COMPRISING ACTINOMYCES VISCOSUS FIMBRIAE

TECHNICAL FIELD

The present invention relates to oral compositions, such as dentifrices and oral solutions, designed to inhibit or prevent the growth of dental plaque on tissues within the oral cavity of a human.

BACKGROUND OF THE INVENTION

The mouth is a habitat for microbial growth and colonization. Within the mouth, the gums, lips, oral mucosa (cheek), palate, tongue and teeth provide surfaces for the colonization and accumulation of bacteria. Teeth are unique in the oral cavity because they have hard, non-shedding surfaces where bacteria and their products (dental plaque) can significantly accumulate, especially in approximal areas and along the gingival crevice.

Dental plaque is a rough sticky film on the oral cavity tissues that is made up of saliva, bacteria and food particles which adheres tenaciously to the tissues, especially to teeth, at points of irregularity or discontinuity. Within a few hours of teeth cleaning, a film of salivary mucus, consisting primarily of proteins, forms a pellicle layer on the teeth and other tissues. Various oral bacteria colonize the mucus and multiply, forming a biofilm of plaque. Carbohydrate food debris adheres to the mucus and is digested by some types of plaque-causing bacteria. The bacterial digestion produces both by-products which add to the plaque accumulation and acid which erodes tooth enamel.

The oral bacteria in dental plaque includes many gram positive and gram negative microorganisms embedded in an extracellular matrix of insoluble polysaccharides, firmly attached to teeth and other oral surfaces. The colonization of bacteria to form dental plaque follows an ecological pattern where a few pioneer species colonize enamel surfaces. More and other bacteria adhere to the pioneers and the plaque progresses through stages of increasing microbial complexity. Mature plaques, often found in protected regions of the teeth, such as cracks, approximal regions and in the gingival crevice, typically contain both aerobes and anaerobes. Saliva and crevicular fluid are a source of nutrients for the dental plaque. Local conditions affect the metabolic activity and composition of dental plaque.

If not prevented or removed, plaque may become embedded with mineral salts, containing calcium and phosphate, to form a hard crusty deposit, calculus or tartar, on the teeth. Calculus may be white or yellowish in color or may be stained or discolored by extraneous agents. Calculus tends to be more unsightly than plaque and much more difficult to remove from the teeth. The toxins in plaque and calculus can irritate the gingival tissues surrounding the coated teeth, causing inflammation and destruction of the gums which can lead to other complications.

Applicant has unexpectedly found that fimbriae from *Actinomyces Viscosus* bacteria inhibit the adherence of *Actinomyces Viscosus* (*A. viscosus*), *Streptococcus sanguis* (*S. sanguis*) and *Porphyromonas gingivalis* (*P. gingivalis*) from adhering to the tissues within the oral cavity, resulting in the prevention and inhibition of dental plaque growth. Applicant has also unexpectedly found that A. viscosus fimbriae reduce the amount of *A. Viscosus, S. sanguis* and *P. gingivalis* already adhering to the oral cavity tissues when the fimbriae are introduced.

SUMMARY OF THE INVENTION

The present invention relates to compositions and methods for inhibiting or preventing growth of dental plaque on tissues within the human oral cavity of a human comprising topical administration, to tissues of a human oral cavity, of a composition comprising a safe and effective amount of *Actinomyces viscosus* fimbriae.

DETAILED DISCLOSURE OF THE INVENTION

The compositions of the present invention comprise a safe and effective amount of *Actinomyces viscosus* fimbriae in a pharmaceutically-acceptable oral carrier.

"Pharmaceutically-acceptable topical oral carrier", as used herein, denotes a carrier for the *A. viscosus* fimbriae comprising solid or liquid filler diluents suitable for use in contact with the oral tissues of humans and lower animals without undue toxicity, incompatibility, instability, irritation, allergic response, and the like, commensurate with a reasonable benefit/risk ratio. Such topical oral carrier, when combined with *A. viscosus* fimbriae, results in a composition which is administered topically to the oral cavity. Preferably such compositions are held in the oral cavity for a period of time, and then largely expectorated rather than being swallowed. Such compositions include mouthwashes, mouth rinses, mouth sprays, dental treatment solutions, toothpastes, dental gels, tooth powders, prophylaxis pastes, lozenges, chewing gums and the like and are more fully described hereinafter. Dentifrices and mouthwashes are the preferred compositions. By the term "fimbriae" is meant the hairlike protein structures, associated proteins, and adhesins, found on the surface of the *A. viscosus* cell.

*A. viscosus* fimbriae can be obtained by the following procedure among others:

1. Twenty liters of *A. viscosus* is grown in Trypticase Soy Broth statically at 37° C. in 2% $CO_2$ for 48 hours.
2. the cells are harvested by centrifugation in a Sorval RC5C centrifuge at 10,000 rpm in a GSA rotor.
3. The resultant cell pellets are washed once with 50 mM Tris/0.15 M NaCl.
4. The resultant pellet is re suspended in 50 mM Tris/0.15 M NaCl plus 0.5 mM PMSF.
5. The cell suspension is passed through a French pressure cell operated at 10,000 psi.
6. The pressed cell suspension is then centrifuged in a RC5C plus at 10,000 rmp in a SA 600 rotor to remove the cell bodies.
7. The resultant supernatant is spun twice in the RC5C plus at 15,000 rpm in a SA 600 rotor to further remove cellular debris.
8. The final fimbriae/adhesin supernatant is adjusted to 20% saturation of ammonium sulfate, and the precipitated fimbriae/adhesin are collected by centrifugation at 30,900 ×g.
9. The ammonium sulfate is removed via dialysis against 50 mM Tris/0.15 M NaCl buffer.

Compositions

Compositions of the present invention preferably comprise aqueous suspensions of *Actinomyces viscosus* fimbriae. Such compositions typically comprise from about 0.001% to about 5% by weight, preferably from about 0.01% to about 1% by weight, more preferably from about 0.1% to about 0.5% by weight of *A. viscosus* fimbriae. For a mouth rinse formulation, the more preferred concentration of *A. viscosus* fimbriae ranges from about 0.01% to about 0.5% by weight. For a lozenge formulation, the more preferred concentration of *A. viscosus* fimbriae ranges from about 0.1% to about 10% by weight. For a chewing gum formulation, the more preferred concentration of *A. viscosus* fimbriae ranges from about 0.1% to about 10% by weight.

By "safe and effective amount" as used herein is meant an amount of compound or composition sufficient to induce a significant positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors.

By the term "comprising", as used herein, is meant that various additional components can be conjointly employed in the compositions of this invention.

Components of the topical, oral carrier are suitable for administration to the oral cavity of a human or lower animal and are compatible with one another and the other components, especially the *A. viscosus* fimbriae, used in an oral composition of the present invention. The term "compatible" as used herein, means that the components are capable of being co-mingled with one another, in a manner such that there is no interaction which would substantially reduce the efficacy of the oral composition under ordinary use conditions. Preferred topical, oral carriers thus provide the desired characteristics for mouthwashes, mouth rinses, mouth sprays, dental treatment solutions, toothpastes, dental gels, toothpowders, prophylaxis pastes, lozenges, chewing gums, and the like. The topical, oral carriers of the present invention comprise components typically used in such compositions which are well known to a skilled practitioner. Such components include, but are not limited to, anticaries agents, antiplaque agents, anticalculus agents, dental abrasives, surfactants, flavoring agents, sweetening agents, binders, humectants, thickening agents, buffering agents, preservatives, coloring agents and pigments, ethanol and water.

Water is an optional component of the topical, oral carriers of the compositions of the present invention. Water employed in the preparation of the commercially suitable compositions should preferably be of low ion content and free of organic impurities. Water preferably comprises from about 2% to about 99%, more preferably from about 20% to about 95% of the compositions of the present invention. When in the form of toothpaste, the compositions preferably comprise from about 2% to about 45%, more preferably from about 30% to about 40%, water, while mouthwashes comprise preferably from about 45% to about 95%, more preferably from about 75% to about 90%, water.

Dental abrasives useful in the topical, oral carriers of the compositions of the present invention include many different materials. The material selected must be one which is compatible with the composition of interest and does not excessively abrade dentine. These include, for example, silicas, including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other materials such as those disclosed by Cooley et al. in U.S. Pat. No. 3,070,510, issued Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For this reason they are preferred for use herein.

The silica abrasive polishing materials useful herein, as well as the other abrasives, generally have an average particle size ranging between about 0.1 and 30 microns, preferably between about 5 and 15 microns. The silica abrasive can be precipitated silica or silica gels such as the silica xerogels described in U.S. Pat. No. 3,538,230, issued Mar. 2, 1970 to Pader et al., and in U.S. Pat. No. 3,862,307, issued Jun. 21, 1975 to DiGiulio, both incorporated herein by reference. Preferred are the silica xerogels marketed under the tradename Syloid® by the W.R. Grace & Company, Davidson Chemical Division. Preferred precipitated silica materials include those marketed by the J. M. Huber Corporation under the tradename, Zeodent®, particularly the silica carrying the designation Zeodent 119®. These silica abrasives are described in U.S. Pat. No. 4,340,583, Wason, issued Jul. 20, 1982, incorporated herein by reference. Other suitable abrasives include alumina and the insoluble metaphosphates such as insoluble sodium metaphosphate (IMP).

Mixtures of abrasives may be used. The total amount of abrasive in the dentifrice embodiments of this invention can range from about 6% to about 70%, preferably from about 15% to about 50%, when the dentifrice is a toothpaste. Higher levels, as high as 90%, may be used if the composition is a tooth powder.

Flavoring agents can also be added to the oral compositions of the present invention to make them more palatable. Suitable flavoring agents include menthol, oil of wintergreen, oil of peppermint, oil of spearmint, oil of sassafras, and oil of clove. Flavoring agents are generally included in the subject compositions in amounts of from about 0% to about 3%, preferably from about 0.04% to about 2% by weight.

Coloring agents may be added to compositions of the present invention to improve appearance. If present, coloring agents typically are included at levels of from about 0.001% to about 0.5% by weight.

Sweetening agents are also preferred in the compositions of the present invention to make them more palatable. Sweetening agents which can be used include aspartame, acesulfame, saccharin salts, dextrose, levulose thaumatin, D-tryptophan, dihydrochalcones, and cyclamate salts. Saccharin salts are preferred. Sweetening agents are generally used in the subject compositions in amounts of from about 0% to about 6%, preferably from about 0.005% to about 5% by weight.

Oral compositions can also contain a surfactant. Suitable surfactants are those which are reasonably stable and form suds throughout a wide pH range, including nonsoap anionic, nonionic, cationic, zwitterionic and amphoteric organic synthetic detergents, and compatible mixtures thereof. Many of these suitable surfactants are disclosed in U.S. Pat. No. 4,051,234, issued to Gieske et al. on Sep. 27, 1977, and in U.S. Pat. No. 3,959,458 issued to Agricola, Briner, Granger and Widder on May 25, 1976, both of which are incorporated herein by reference. Surfactants are typically present in compositions of the present invention at a level of from 0% to about 10%, preferably from about 0.2% to about 4% by weight. Surfactants may also be used as solubilizing agents to help retain sparingly soluble components, e.g., some flavoring agents, in solutions. Surfactants suitable for this purpose include polysorbates and poloxamers.

In preparing oral compositions of the present invention, it is desirable to add binders and/or thickening agents, particularly to toothpaste compositions. Preferred binders and thickening agents include for example, carboxyvinyl polymers, polysaccharide gums such as xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. These binders and thickening agents are generally present in the compositions of the present invention in amounts of from about 0% to about 6%, preferably from about 0.1% to about 5% by weight.

Another optional component of the oral carriers of the compositions of the present invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 2% to about 55%, by weight of the compositions herein. Suitable humectants for use in compositions of the present invention include edible polyhydric alcohols such as glycerin, sorbitol, xylitol, polyethylene glycol, and propylene glycol, especially sorbitol and glycerin.

Opacifiers may also be used in toothpastes of the present invention to render the toothpaste opaque. Suitable opacifiers include titanium dioxide and some abrasives including, for example, magnesium aluminum silicate. Opacifiers generally comprise from about 0% to about 4%, preferably from about 0.5% to about 3% by weight of the compositions herein.

Other optional components of the compositions of the present invention are preservatives. The preservatives prevent microbial growth in the compositions. Suitable preservatives include methylparaben, propylparaben, benzoates and ethanol. If the preservative is ethanol, it generally comprises from 0% to about 35% by weight, preferably from about 5% to about 15%, of the compositions herein. Other preservatives generally comprise from about 0% to about 5% by weight, preferably from about 0.1% to about 2%, of the compositions herein.

Antimicrobial, antiplaque agents can also optionally be present in the oral compositions of the present invention, on the condition that they are compatible with the *A. viscosus* fimbriae. Such agents may include, but are not limited to, triclosan, 2,4,4'-trichloro-2'-hydroxydiphenyl ether, as described *The Merck Index,* 11th Ed. (1989), p. 1520 (entry No. 9573); in U.S. Pat. No. 3,506,720; and in Eur. Pat. Appl. No. 0,251,591 of Beecham Group, PLC, published Jan. 7, 1988, chlorhexidine, (Merck Index, No. 2090), alexidine (Merck Index, No. 222); hexetidine (Merck Index, No. 4624); sanguinarine (Merck Index, No. 8320); benzalkonium chloride (Merck Index, No. 1066); salicylanilide (Merck Index, No. 8299); domiphen bromide (Merck Index, No. 3411); cetylpyridinium chloride, (CPC) (Merck Index, No. 2024); tetradecylpyridinium chloride, (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as cylium peroxide, hydrogen peroxide, and magnesium monoperthalate and its analogs as described in U.S. Pat. No. 4,670,252; and analogs and salts of the above antimicrobial antiplaque agents. If present, the antimicrobial antiplaque agents may comprise from about 0% to about 6%, preferably from about 0.1% to about 5% by weight of the compositions of the present invention.

Anti-inflammatory agents can also be present in the oral compositions of the present invention. Such agents may include, but are not limited to, non-steroidal anti-inflammatory agents such as ketorolac, flurbiprofen, ibuprofen, naproxen, indomethacin, aspirin, ketoprofen, piroxicam and meclofenamic acid. If present, the anti-inflammatory agents generally comprise from about 0.001% to about 5% by weight of the compositions of the present invention.

Nutrients can also be present in the oral composition of the present invention, on condition that they are compatible with the *A. viscosus* fimbriae. Such agents may include folate, retinoids (Vitamin A), Vitamin C, Vitamin E and zinc. If present, the nutrients generally comprise from about 0.001% to about 10% by weight of the compositions of the present invention.

Other optional ingredients include a safe and effective amount of a fluoride ion source, which typically is in the form of a water-soluble fluoride compound. This water-soluble fluoride compound is typically present in the compositions of the present invention in an amount sufficient to give a fluoride concentration of from about 0.0025% to about 5.0% by weight, preferably from about 0.005% to about 2.0% by weight. Preferred fluoride sources are sodium fluoride, acidulated phosphate fluoride, and sodium monofluorophosphate. U.S. Pat. No. 3,678,154, issued Jul. 18, 1972 to Widder et al., the disclosure of which is incorporated herein by reference, discloses such salts as well as others.

Compositions of the present invention may also include one or more anticalculus agents, on the condition that they are compatible with the *A. viscosus* fimbriae. Anticalculus agents which may be useful in the compositions of the present invention include diphosphonates such as 1-azocycloheptane-2,2-diphosphonate AHP) and ethane-1-hydroxy-1,1-diphosphonate (EHDP), sodium zinc citrate, phosphocitrate, tripolyphosphate, and linear polycarboxylate (LPC); pyrophosphates or polyphosphates such as those disclosed in U.S. Pat. No. 4,590,066 issued to Parran & Sakkab on May 20, 1986 (e.g. tetrasodium pyrophosphate, tetrapotassium pyrophosphate, and dihdrogen disodium pyrophosphate); polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. If present, the anticalculus agents generally comprise from about 0.2% to about 13%, preferably from about 0.4% to about 6% of the compositions of the present invention. Preferred anticalculus agents are pyrophosphate and AHP.

Preferred compositions of the present invention are in the form of toothpastes. Components of such toothpastes generally include a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0:3% as fluoride ion), an anticalculus agent (from about 0.1% to about 13%), and an antiplaque agent (from about 0.1% to about 5%).

Other preferred compositions of the present invention are mouthwashes and mouth sprays. Components of such mouthwashes and mouth sprays include water. (from about 45% to about 95%), ethanol (from about 0% to about 25%), a humectant (from about 0% to about 50%), a surfactant agent (from about 0.01% to about 7%), an flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), an anticalculus agent (from about 0.1% to about 3%), and an antiplaque agent (from about 0.1% to about 5%).

Other preferred compositions of the present invention are dental solutions. Components of such dental solutions generally include water (from about 90% to about 99%), preservative (from about 0.01% to about 0.5%), thickening agent (from about 0% to about 5%), flavoring agent (from about 0.04% to about 2%), sweetening agent (from about 0.1% to about 3%), and surfactant (from 0% to about 5%).

Other preferred compositions may be non-aqueous mouth rinses. Suitable components are disclosed in U.S. Pat. No. 4,312,889 issued Jan. 26, 1982 to Melsheimer, and in U.S. Pat. No. 5,143,720 issued Sept. 1, 1992 to Lopes, both incorporated herein by reference. Alcohol free mouth rinses are also preferred. Suitable compositional components can disclosed in U.S. Pat. No. 4,919,918, issued Apr. 24, 1990 to Cole et al., in U.S. Pat. No. 5,283,056, issued Feb. 1, 1994 to Chung et al., in U.S. Pat. No. 5,284,648, issued Feb. 8, 1994 to White et al., and in PCT Appl. No. 9 401 081, published Jan. 20, 1990 and having a U.S. patent application equivalent, each incorporated herein by reference.

Other embodiments of the oral compositions herein include lozenges. Suitable lozenge components (e.g. a candy base) are disclosed in U.S. Pat. No. 4,931,473, issued Jun. 5. 1990, to Kelleher et al., and in U.S. Pat. No. 4,139,627, issued Feb. 13, 1979 to Lane et al., and in PCT Appl. No. 9 401 081, of Konopa, published Jan. 20, 1994, each incorporated herein by reference..

Other preferred compositions include chewing gums. Chewing gum components (e.g. gum base, flavoring and sweetening agents) are disclosed in U.S. Pat. No. 4,083,955, issued Apr. 11, 1978 to Grabenstetter et al., the disclosure of which is incorporated herein by reference.

The pH of the subject compositions and/or its pH in the mouth can be any pH which is safe for the mouth's hard and soft tissues. Such pH's are generally from about 3 to about 10, more preferably from about 4 to about 8.

Methods of Use

Another aspect of the present invention involves methods for inhibiting or preventing growth of dental plaque on tissues within the oral cavity comprising topical administration, to tissues of the oral cavity, of a composition comprising a safe and effective amount of *Actinomyces viscosus* fimbriae. Such compositions are described hereinabove.

These methods involve administering a safe and effective amount of *A. viscosus* fimbriae typically by administering an oral composition of the present invention, as described hereinabove to the oral cavity. Generally an amount of at least about 5 mg of *A. viscosus* fimbriae is effective. The teeth and other oral cavity tissues are "bathed" in the *A. viscosus* fimbriae.

When the oral composition is a toothpaste, typically from about 0.3 grams to about 15 grams, preferably from about 0.5 grams to about 5 grams, more preferably from about 1 to about 2 grams, of toothpaste is applied to an applicating device e.g., a toothbrush. The applicating device is then contacted with the oral cavity surfaces in a manner such that the oral composition is contacted with tissue of the oral cavity, especially the teeth and gums. The applicating device may be further used to effect an even distribution of the oral composition to the tooth surface, for example by brushing. The application preferably lasts for a period of from about 15 seconds to about 10 minutes, more preferably from about 1 minute to about 2 minutes. Following application, the toothpaste residue is typically removed from the tooth surface by using a liquid acceptable to the oral cavity, typically water, to rinse the oral cavity.

When the oral composition is a mouthwash, typically from about 1 ml. to about 20 ml, preferably from about 2 ml to about 15 ml., most preferably from about 10 ml to about 15 ml, of liquid mouthwash containing the antiplaque *A. viscosus* fimbriae is introduced to the oral cavity. The liquid mouthwash is then agitated for from about 10 seconds to about 30 min., preferably from about 15 seconds to about 3 min., more preferably from about 30 seconds to about 2 minutes, within the oral cavity to obtain an improved distribution of the mouthwash over the tissue of the oral cavity. Following agitation, the mouthwash is typically expectorated from the oral cavity.

Application frequency is preferably from about once daily to about 4 times daily, more preferably from about 3 times weekly to about 3 times daily, more preferably still from about once to about twice daily. The period of such treatment typically ranges from about one day to a lifetime.

ORAL COMPOSITION EXAMPLES

The following non-limiting examples illustrate representative oral compositions containing active agents of the present invention. The compositions are made using conventional processes.

EXAMPLE I

The following representative example of a toothpaste composition of the present invention is made by conventional processes by mixing the following:

| Component | % by weight |
| --- | --- |
| Sorbitol | 42 |
| Saccharin Sodium | 0.13 |
| FD&C Blue (1% Soln) | 0.05 |
| Precipitated Silica | 20 |
| Sodium Fluoride | 0.24 |
| Flavor | 0.9 |
| Sodium Alkyl Sulfate | 1 |
| Phosphoric Acid | 0.4 |
| Carbomer 940 | 0.25 |
| Xanthan Gum | 0.5 |
| Titanium Dioxide | 0.5 |
| *A. viscosus* fimbriae | 0.5 |

| Component | % by weight |
|---|---|
| Purified Water | q.s. |

EXAMPLE II

The following representative toothpaste composition of the present invention is made by conventional processes by mixing the following:

| Component | % by weight |
|---|---|
| Sorbitol | 35 |
| Saccharin Sodium | 0.2 |
| FD&C Blue (1% Soln) | 0.05 |
| Precipitated Silica | 25 |
| Sodium Fluoride | 0.24 |
| Flavor | 1.5 |
| Sodium Alkyl Sulfate | 1.2 |
| Carbomer 940 | 0.25 |
| Xanthan Gum | 0.65 |
| Titanium Dioxide | 0.5 |
| *A. viscosus* fimbriae | 1 |
| Purified Water | q.s. |

EXAMPLE III

The following representative example of a mouth rinse composition of the present invention is made by conventional processes by mixing the following:

| Component | % by weight |
|---|---|
| *A. viscosus* fimbriae | 0.1 |
| Ethanol | 12 |
| Glycerin | 10 |
| Dibasic Sodium Phosphate heptahydrate | 0.07 |
| Saccharin Sodium | 0.08 |
| Monobasic Sodium Phosphate monohydrate | 2.03 |
| Polysorbate 80 | 0.33 |
| FD&C Blue (1% Soln) | 0.02 |
| Flavor | 0.15 |
| Purified Water | q.s. |

EXAMPLE IV

The following representative example of a mouthwash composition of the present invention is made by conventional processes by mixing the following:

| Component | % by weight |
|---|---|
| *A. viscosus* fimbriae | 0.2 |
| Saccharin Sodium | 0.05 |
| Polysorbate 80 | 0.3 |
| Methyl paraben | 0.2 |
| Propyl paraben | 0.1 |
| Flavor | 0.1 |
| Purified Water | q.s. |

EXAMPLE V

The following is a representative example of a lozenge composition of the present invention. The lozenge can be made by conventional processes.

| Component | % by weight |
|---|---|
| *A. viscosus* fimbriae | 1.2 |
| Sorbitol | 90.5 |
| Hydroxypropyl cellulose | 5 |
| Flavor | 0.8 |
| Magnesium Stearate | 2.5 |

EXAMPLE VI

The following is a representative example of a chewing gum composition of the present invention. The chewing gum can be made by conventional processes.

| Component | % by weight |
|---|---|
| Gum Base | 20 |
| Plasticizer | 2 |
| Sorbitol Solution | 20 |
| Glycerin | 10 |
| Sweetener | 1 |
| *A. viscosus* fimbriae | 1 |
| Flavor | 1 |
| Sorbitol powder | q.s. |

While particular embodiments of the present invention have been described, it will be obvious to those skilled in the art that various changes and modifications to the present invention can be made without departing from the spirit and scope of the invention. It is intended to cover, in the appended claims, all such modifications that are within the scope of the present invention.

What is claimed is:

1. A method for inhibiting or preventing growth of dental plaque by blocking or reducing the adherence of *Actinomyces viscosus*, *Streptococcus sanguis*, and *Porphyromonas gingivalis* to tissues within the human oral cavity comprising topical administration, to tissues of a human oral cavity, of a composition comprising a safe and effective amount of *Actinomyces viscosus* fimbriae.

2. The method of claim 1 for inhibiting or preventing growth of dental plaque on tooth surfaces within the oral cavity of a human comprising topical administration, to tooth surfaces of a human oral cavity, of a composition comprising a safe and effective amount of *Actinomyces viscosus* fimbriae.

3. The method of claim 1 wherein the composition comprises from about 0.01% to about 5% of *Actinomyces viscosus* fimbriae.

4. A dentifrice composition to inhibit or prevent growth of dental plaque by blocking or reducing the adherence of *Actinomyces viscosus*, *Streptococcus sanguis*, and *Porphyromonas gingivalis* to tooth surfaces within the oral cavity of a human, comprising:

(a) a safe and effective amount of *Actinomyces viscosus* fimbriae; and (b) a dentifrice carrier comprising a dental abrasive and a flavoring or sweetening agent.

5. The composition of claim 4 wherein the composition is a toothpaste comprising a surfactant, a humectant, and water.

6. The composition of claim 4 wherein the composition comprises a safe and effective amount of a fluoride anticaries agent.

7. The composition of claim 5 wherein the composition comprises a safe and effective amount of an anticalculus agent.

8. The composition of claim 5 wherein the composition comprises a safe and effective amount of an anticalculus agent and a fluoride anticaries agent.

9. The composition of claim 5 wherein the composition comprises a safe and effective amount of an antimicrobial antiplaque agent.

10. The composition of claim 5 wherein the composition comprises a safe and effective amount of a non-steroidal anti-inflammatory agent.

11. The composition of claim 5 wherein the composition comprises from about 0.1% to about 1% of the *Actinomyces viscosus* fimbriae.

12. A mouthwash or mouth spray composition comprising:
 (a) a safe and effective amount of *Actinomyces viscosus* fimbriae; and
 (b) a carrier comprising a flavoring or sweetening agent.

13. The composition of claim 12 wherein the composition is a solution comprising a surfactant.

14. The composition of claim 13 wherein the composition comprises a humectant and water.

15. The composition of claim 13 wherein the composition comprises ethanol.

16. The composition of claim 13 wherein the composition comprises a safe and effective amount of a fluoride anticaries agent.

17. The composition of claim 13 wherein the composition comprises a safe and effective amount of an antimicrobial antiplaque agent.

18. The composition of claim 13 wherein the composition comprises a safe and effective amount of a non-steroidal anti-inflammatory agent.

19. The composition of claim 13 wherein the composition comprises from about 0.01% to about 0.5% *Actinomyces viscosus* fimbriae.

20. An oral care composition to inhibit or prevent growth of dental plaque by blocking or reducing the adherence of *Actinomyces viscosus, Streptococcus sanguis*, and *Porphyromonas gingivalis* to tooth surfaces within the oral cavity of a human, comprising:
 (a) a safe and effective amount of *Actinomyces viscosus* fimbriae; and
 (b) an carrier comprising a flavoring or sweetening agent.

* * * * *